United States Patent
Aurin et al.

(10) Patent No.: US 12,220,557 B2
(45) Date of Patent: *Feb. 11, 2025

(54) BLADDER FOR AN INFUSION ASSEMBLY

(71) Applicant: Avent, Inc., Alpharetta, GA (US)

(72) Inventors: Gary D. Aurin, Foothill Ranch, CA (US); Travis W. Klyber, Roswell, GA (US); Thad R. Hmielak, Minneapolis, MN (US)

(73) Assignee: Avent, Inc., Alpharetta, GA (US)

( * ) Notice: Subject to any disclaimer, the term of this patent is extended or adjusted under 35 U.S.C. 154(b) by 415 days.

This patent is subject to a terminal disclaimer.

(21) Appl. No.: 17/673,989

(22) Filed: Feb. 17, 2022

(65) Prior Publication Data
US 2022/0273867 A1 Sep. 1, 2022

Related U.S. Application Data

(63) Continuation of application No. 16/485,872, filed as application No. PCT/US2017/018586 on Feb. 20, 2017, now Pat. No. 11,253,644.

(51) Int. Cl.
*A61M 5/152* (2006.01)
(52) U.S. Cl.
CPC ..... *A61M 5/152* (2013.01); *A61M 2205/0216* (2013.01); *A61M 2205/3337* (2013.01)
(58) Field of Classification Search
CPC .............. A61M 5/148; A61M 5/14586; A61M 2205/02; A61M 2205/0216; A61M 2205/3337; A61M 5/145; A61M 5/152
See application file for complete search history.

(56) References Cited

U.S. PATENT DOCUMENTS

| 3,506,005 A | 4/1970 | Gilio et al. |
| 3,698,595 A | 10/1972 | Gortz et al. |
| (Continued) | | |

FOREIGN PATENT DOCUMENTS

| DE | 102004030361 A1 | 1/2006 |
| EP | 0933091 A2 | 8/1999 |
| (Continued) | | |

OTHER PUBLICATIONS

International Search Report and Written Opinion for PCT/US2017/018586, dated Oct. 27, 2017, 12 pages.

*Primary Examiner* — Jason E Flick
(74) *Attorney, Agent, or Firm* — Meunier Carlin & Curfman LLC

(57) ABSTRACT

Bladders and elastomeric pumps for infusion assemblies are provided. For example, a bladder may comprise a body extending over a length from a first end to an opposing second end; an outer diameter; an inner diameter; and a wall thickness. The wall thickness may gradually transition from a first wall thickness at the first end to a second wall thickness at the second end. In other embodiments, the wall thickness at a midpoint of the length is different than the wall thickness at each of the first end and the second end. An elastomeric pump may comprise an inflatable elastomeric bladder and a mandrel. The bladder includes a body extending over a bladder length from a first bladder end to an opposing second bladder end and a wall thickness, which is different at a midpoint of the bladder length than at each of the first and second bladder end.

20 Claims, 14 Drawing Sheets

(56) References Cited

U.S. PATENT DOCUMENTS

| | | | |
|---|---|---|---|
| 3,876,115 A | 4/1975 | Venus, Jr. et al. | |
| 4,055,201 A | 10/1977 | Fowler et al. | |
| 4,953,753 A | 9/1990 | Gortz | |
| 4,991,593 A | 2/1991 | LeVahn | |
| 5,061,243 A | 10/1991 | Winchell et al. | |
| 5,120,315 A | 6/1992 | Hessel | |
| 5,263,935 A * | 11/1993 | Hessel | A61M 5/152 604/131 |
| 5,284,481 A | 2/1994 | Soika et al. | |
| 5,306,257 A * | 4/1994 | Zdeb | A61M 5/14586 604/251 |
| 5,390,738 A | 2/1995 | Eslinger et al. | |
| 5,433,709 A | 7/1995 | Kriesel | |
| 5,462,208 A | 10/1995 | Stahley et al. | |
| 5,529,214 A | 6/1996 | Lasonde et al. | |
| 5,655,569 A | 8/1997 | Tackett | |
| 6,361,840 B2 | 3/2002 | Nelson et al. | |
| 7,523,764 B2 | 4/2009 | Lepola et al. | |
| 7,678,075 B2 | 3/2010 | Wantink et al. | |
| 7,704,230 B2 | 4/2010 | Chatlynne et al. | |
| 8,002,763 B2 | 8/2011 | Berthiaume et al. | |
| 9,186,488 B2 | 11/2015 | Tilson et al. | |
| 9,316,403 B2 | 4/2016 | Haws | |
| 2004/0138627 A1 | 7/2004 | Forrest | |
| 2006/0229558 A1* | 10/2006 | Heston | A61M 5/152 604/131 |
| 2012/0041422 A1 | 2/2012 | Whiting et al. | |
| 2013/0211333 A1 | 8/2013 | Tefera et al. | |
| 2014/0058194 A1 | 2/2014 | Soletti et al. | |
| 2014/0276147 A1 | 9/2014 | Gloth et al. | |
| 2016/0144105 A1 | 5/2016 | Hooven et al. | |
| 2016/0158014 A1 | 6/2016 | Daniel | |

FOREIGN PATENT DOCUMENTS

| | | |
|---|---|---|
| EP | 3006063 A1 | 4/2016 |
| EP | 3582828 B1 | 12/2019 |
| WO | 9924106 A1 | 5/1999 |
| WO | 0013734 A2 | 3/2000 |
| WO | 0107102 A2 | 2/2001 |
| WO | 2018151736 A1 | 8/2018 |

* cited by examiner

BLADDER FOR AN INFUSION ASSEMBLY

CROSS-REFERENCE TO RELATED APPLICATIONS

The present application claims priority to and the benefit of U.S. patent application Ser. No. 16/485,872, filed Aug. 14, 2019, which is a 371 National Phase entry of PCT Patent Application No. PCT/US17/18586, filed on Feb. 20, 2017, each of which is incorporated herein by reference in their entireties.

BACKGROUND

The present invention relates to liquid dispensing apparatus and pertains particularly to bladders for elastomeric infusion assemblies.

Often, patients are intravenously supplied with pharmaceutically active liquids at a controlled rate over a long period of time. Preferably, such infusion is accomplished while the patient is in an ambulatory state. A few devices have been developed in the past for accomplishing this purpose.

Typically, an infusion assembly includes an inflatable elastomeric bladder forming a liquid container that is supported by a mandrel, as well as a flow control valve or device and tubing for supply of the liquid to the patient. The walls of the bladder are forced to expand when filled with the liquid and provide the pressure for expelling the liquid. Usually, conventional infusion assemblies are filled by hand by means of a syringe, which often requires an inordinate amount of force. Another drawback to the prior art assemblies is that such assemblies provide pressures and flow rates that can vary widely with the volume of liquid therein. Therefore, conventional assemblies do not have a reasonably stable pressure and flow rate over the infusion period. In addition, conventional bladders frequently have difficulty dispensing substantially all of the liquid by the end of the infusion period, and it is undesirable to have liquid remaining in the bladder.

Accordingly, infusion assemblies that overcome one or more drawbacks of known infusion assemblies would be desirable. In particular, infusion assemblies having mandrel and/or bladder configurations that improve consistency in the pressure and flow rate provided by the assembly would be beneficial. For example, modifying the mandrel outer diameter to reduce the crack and/or fill pressure and/or to decrease the residual volume of liquid at the end of an infusion period would be advantageous. As another example, modifying a wall thickness of the bladder such that the wall thickness is non-uniform to reduce crack and/or fill pressure and/or to provide more consistent infusion pressure and flow rate would be helpful.

SUMMARY

Aspects and advantages of the invention will be set forth in part in the following description, or may be obvious from the description, or may be learned through practice of the invention.

In one aspect, the present subject matter is directed to an elastomeric bladder for an elastomeric pump. The bladder comprises a body extending over a length from a first end to an opposing second end; an outer diameter; an inner diameter; and a wall thickness. The wall thickness gradually transitions from a first wall thickness at the first end to a second wall thickness at the second end.

It should be appreciated that the bladder may be further configured with any of the additional features as described herein. For instance, in some embodiments, the wall thickness at the first end is greater than the wall thickness at the second end. In other embodiments, the wall thickness at the second end is greater than the wall thickness at the first end. The outer diameter of the bladder may be constant over the length. Further, the inner diameter may gradually transition from a first inner diameter at the first end to a second inner diameter at the second end.

In another aspect, the present subject matter is directed to an elastomeric bladder for an elastomeric pump. The bladder comprises a body extending over a length from a first end to an opposing second end; an outer diameter; an inner diameter; and a wall thickness. The wall thickness at a midpoint of the length is different than the wall thickness at each of the first end and the second end.

It should be appreciated that the bladder may be further configured with any of the additional features as described herein. For example, in some embodiments, the wall thickness at the midpoint of the length is less than the wall thickness at each of the first end and the second end such that the wall thickness tapers from each of the first end and the second end toward the midpoint. The outer diameter may be constant over the length. Further, in some embodiments, the inner diameter increases from each of the first end and the second end toward the midpoint. Moreover, each of the first end and the second end may define a groove about an outer perimeter of the bladder for receipt of an O-ring.

In yet another aspect, the present subject matter is directed to an elastomeric pump for an infusion assembly. The elastomeric pump comprises an inflatable elastomeric bladder and a mandrel. The bladder includes a body extending over a bladder length from a first bladder end to an opposing second bladder end, a bladder outer diameter, a bladder inner diameter, and a wall thickness. The bladder is disposed on the mandrel and is sealingly secured on the mandrel near each of the first bladder end and the second bladder end. Further, the wall thickness at a midpoint of the bladder length is different than the wall thickness at each of the first bladder end and the second bladder end.

It should be appreciated that the elastomeric pump may be further configured with any of the additional features as described herein. As an example, in some embodiments, the wall thickness at the first bladder end is greater than the wall thickness at the second bladder end. In other embodiments, the wall thickness at the second bladder end is greater than the wall thickness at the first bladder end. In still other embodiments, the wall thickness at the midpoint of the bladder length is less than the wall thickness at each of the first bladder end and the second bladder end such that the wall thickness tapers from each of the first bladder end and the second bladder end toward the midpoint of the bladder length. Moreover, each of the first bladder end and the second bladder end may define a groove about an outer perimeter of the bladder for receipt of an O-ring that secures the bladder to the mandrel.

Additionally, the mandrel may include a mandrel body extending over a mandrel length from a first mandrel end to an opposing second mandrel end, as well as a mandrel outer diameter. In some embodiments, the mandrel outer diameter at a midpoint of the mandrel length is greater than the mandrel outer diameter at each of the first mandrel end and the second mandrel end such that the mandrel is a generally convex mandrel. In some instances of such embodiments, the wall thickness of the bladder at the midpoint of the bladder length may be less than the wall thickness at each of the first bladder end and the second bladder end such that the wall thickness tapers from each of the first bladder end and the second bladder end toward the midpoint of the bladder length.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
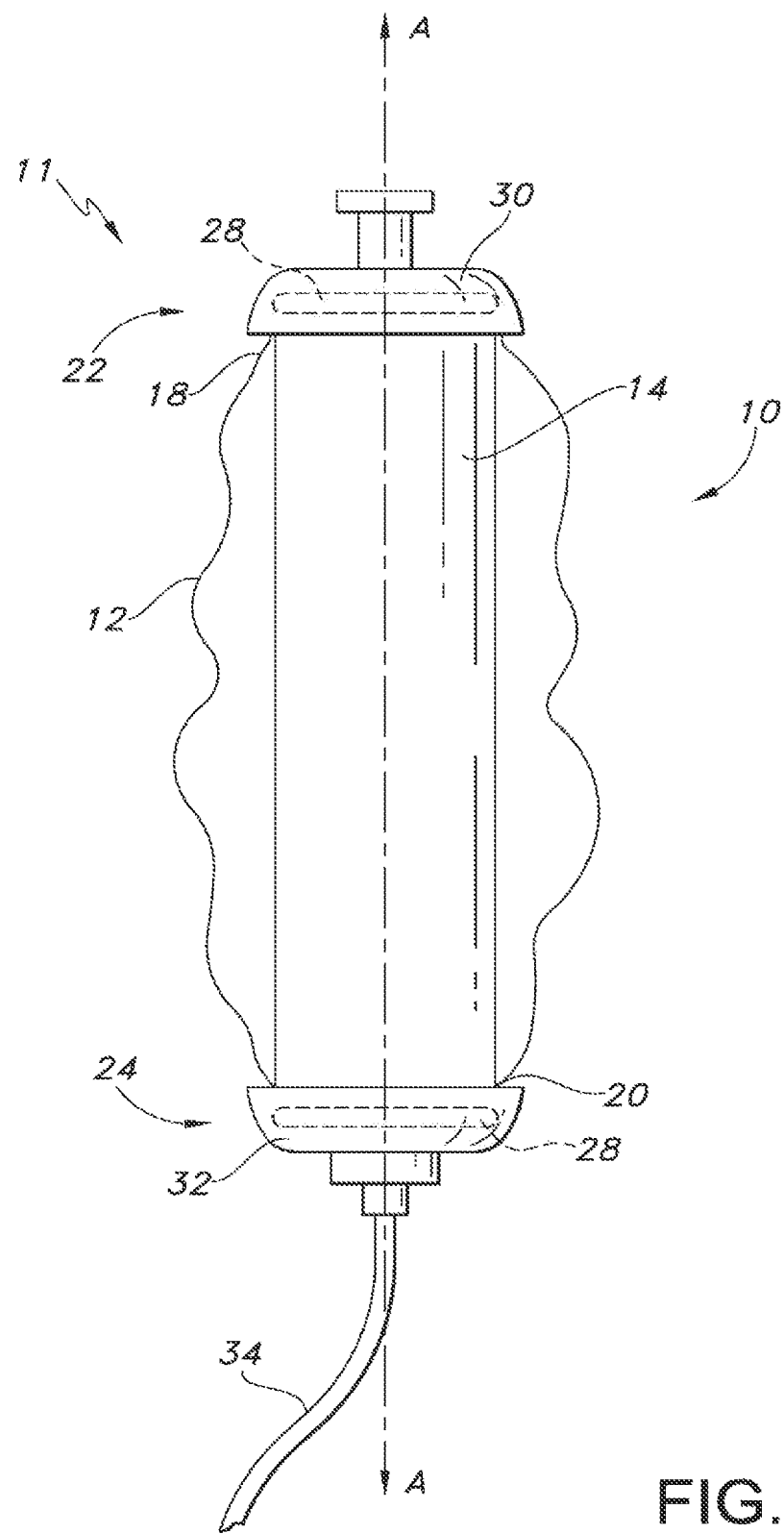
FIG. 1 is a side view of an infusion assembly having a protective housing or shell according to an exemplary embodiment of the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Moreover, the particular naming of the components, capitalization of terms, the attributes, data structures, or any other programming or structural aspect is not mandatory or significant, and the mechanisms that implement the invention or its features may have different names, formats, or protocols. Also, the particular division of functionality between the various components described herein is merely exemplary and not mandatory; functions performed by a single component may instead be performed by multiple components, and functions performed by multiple components may instead performed by a single component.

Further, the detailed description uses numerical and letter designations to refer to features in the drawings. Like or similar designations in the drawings and description have been used to refer to like or similar parts of the invention. As used herein, the terms "first," "second," and "third" may be used interchangeably to distinguish one component from another and are not intended to signify location or importance of the individual components.

Figure 2:
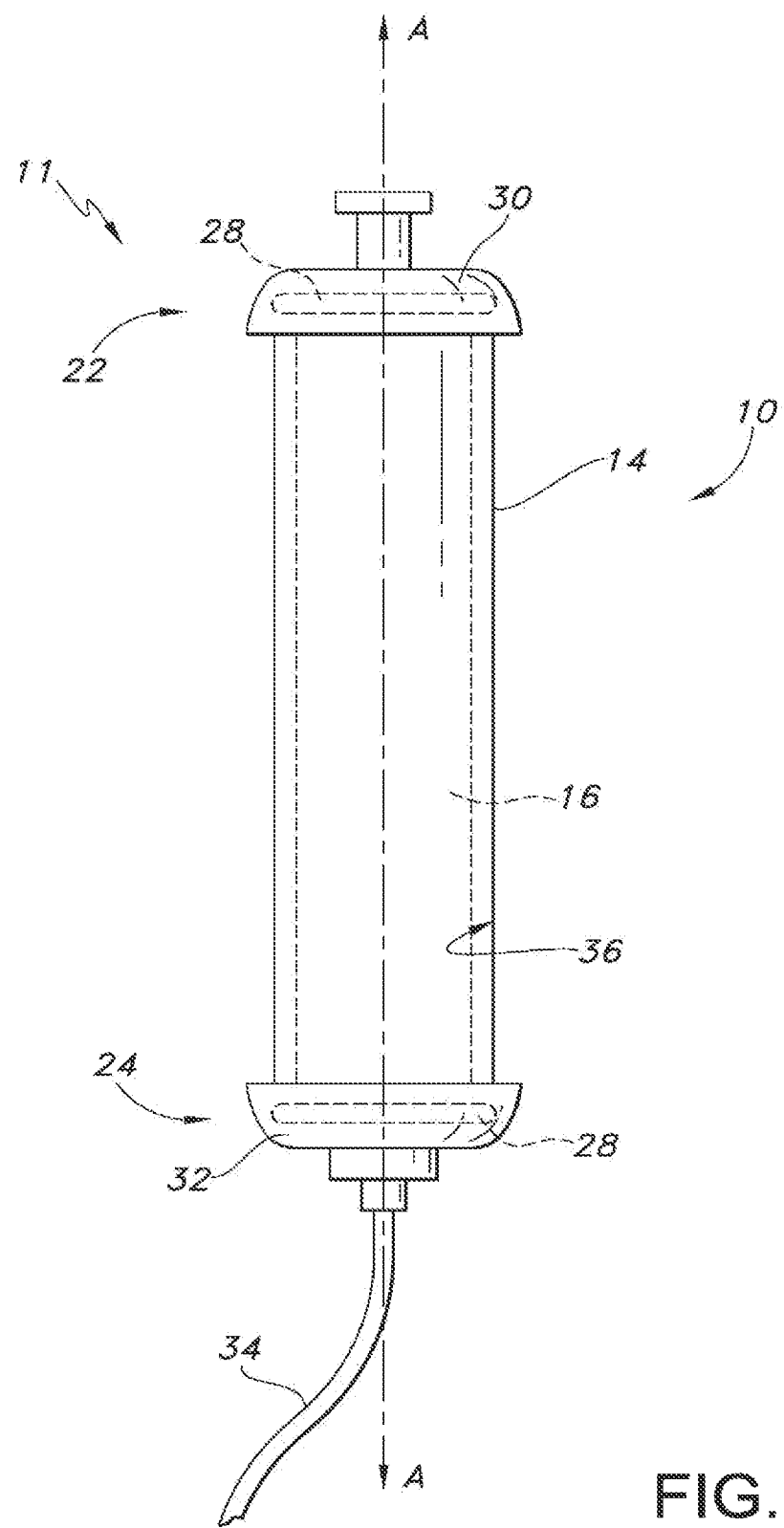
FIG. 2 is a side view of the infusion assembly of FIG. 1, with the protective housing or shell omitted.

Referring to the drawings, FIGS. 1 and 2 illustrate an exemplary embodiment of an elastomeric pump for an infusion assembly in accordance with the present subject matter. The elastomeric infusion pump 10 of infusion assembly 11 comprises an outer collapsible substantially non-stretchable housing or shell 12, protectively mounted over a reservoir 14, and a support member 16. More particularly, the collapsible housing 12 has a substantially spherical configuration for confining and guiding an inflatable reservoir or bladder 14 into a concentric position around a central support member or mandrel 16, enabling the bladder 14 to expand naturally in a spherical configuration as will be described. The collapsible housing 12 has coaxial openings defined by tubular sleeve extensions 18, 20 through which ends of the mandrel 16 extend. The collapsible housing 12 may be, e.g., a non-stretch blow molded housing of from five to ten mils in thickness and made of a material such as polyurethane, PVC film, and/or polyethylene that is transparent. This forms a simple, inexpensive, compact unit with a certain amount of protection for the elastic reservoir. Certain applications may require a tougher collapsible housing 12. In such cases, the housing 12 should be transparent, UV stable, flexible, and highly resistant to puncturing, e.g., the housing 12 may be constructed of a material such as tough composites in a flexible form such as a fabric such as the material available under the trademark Kevlar.

The bladder 14, which is an inflatable reservoir, is mounted on the mandrel 16, e.g., using a press fit or a clearance fit. The bladder 14 may be a single sleeve or multiple sleeves, e.g., the bladder 14 may comprise an inner sleeve that is a chemically inert sleeve and an outer sleeve or sleeves that are highly elastic. The bladder 14 will be described in greater detail below.

The central support member or mandrel 16 has a first end 22 and a second end 24, and the mandrel 16 includes circular grooves 26 (FIGS. 3, 4) at each end 22, 24 thereof into which portions of the sleeve 14 and housing 12 are biased by means of a pair of O-rings 28. More particularly, an O-ring 28 secures the bladder 14 to the mandrel 16 at each of the first and second ends 22, 24 of the mandrel 16. Each O-ring 28 fits into the groove 26 at the respective mandrel end 22, 24 such that the bladder 14 is secured between the O-ring 28 and the groove 26 at each mandrel end 22, 24. Further, the first end 22 includes a first cup-shaped cap 30, and the second end 24 includes a second cup-shaped cap 32. First and second caps 30, 32 extend over and protectively cover the O-ring connections for clamping the bladder 14 and housing 12 to the mandrel 16. In exemplary embodiments, the caps 30, 32 are releasably coupled to the ends 22, 24. The infusion assembly 11 further includes a tubing set, having a tube 34 having a filter (not shown) and a connector (not shown) at a distal tube end, that extends from the second end 24 of the mandrel 16 to provide a means for connecting and dispensing a fluid to a site, such as a vein of a patient.

It will be appreciated that the bladder 14 expands and contracts to receive and dispense a fluid. Pressure acts on the fluid as it is injected into the bladder 14 to expand the bladder from an initial unexpanded state to a maximum expanded state. The maximum expanded state accommodates a fill volume. Typically, the fluid is injected from a syringe-type device and passes through a one-way valve connector before it enters the bladder, and the pressures upstream of the one-way valve connector generally are greater than the pressures within the bladder. As such, the upstream pressures move the liquid through the valve connector, then through one end of the mandrel 16, through a port in the mandrel, and against an inner surface 36 of the bladder 14. The crack pressure indicates the force that must be transmitted by the fluid to overcome the initial resistance to expansion of the inflatable bladder 14. The fill pressure indicates the forces required for gradual expansion of the bladder 14 between its ends attached to the mandrel 16; the expansion is generally in a radial direction with respect to a central axis A of the pump 10. The fill pressures initially decrease from the maximum crack pressure and then increase to a maximum when the fill volume is achieved.

Figure 3:
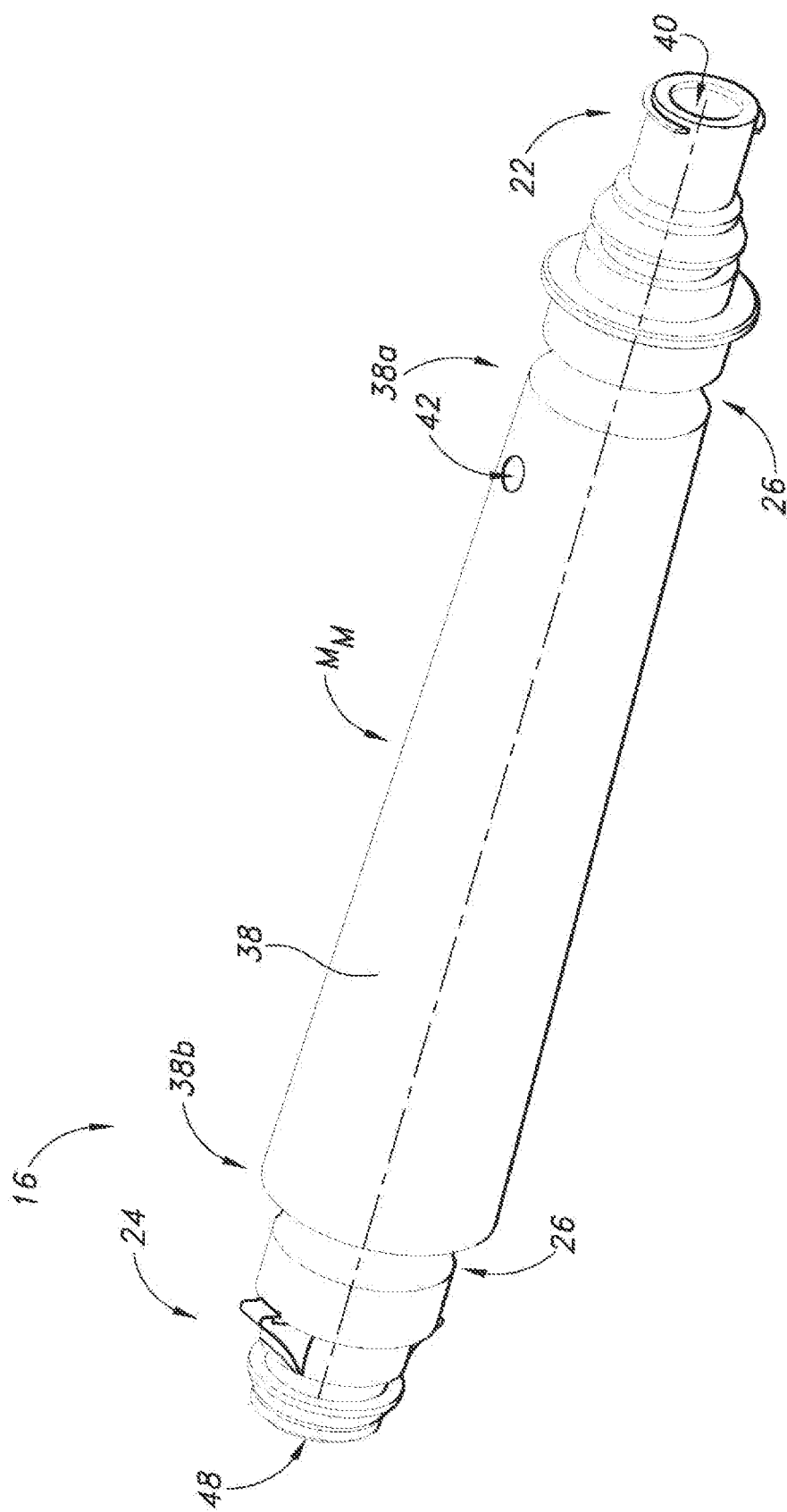
FIG. 3 is a perspective view of a mandrel of an infusion assembly according to an exemplary embodiment of the present subject matter.
Figure 4:
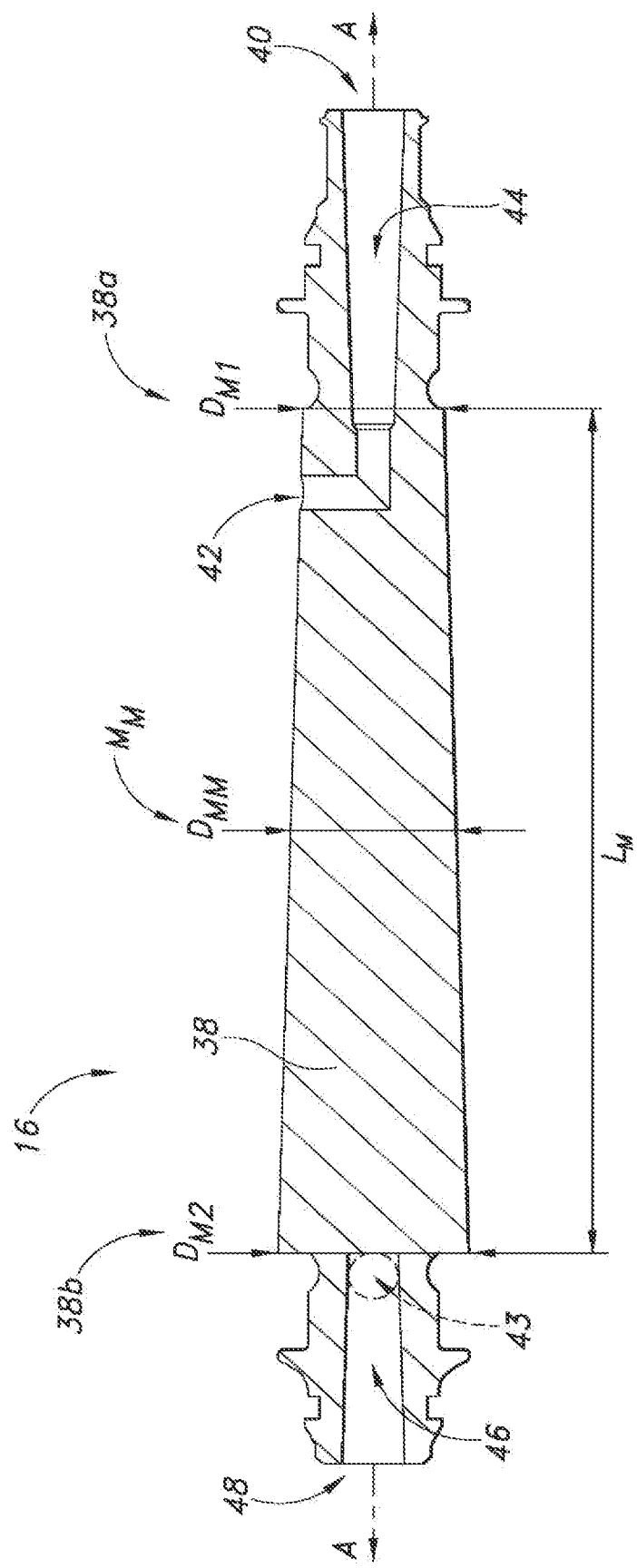
FIG. 4 is a cross-section view of the mandrel of FIG. 3.

Referring now to FIGS. 3 and 4, a perspective view and a cross-section view are provided of a mandrel 16 according to an exemplary embodiment of the present subject matter. As shown in the depicted embodiment, the mandrel 16 has a body 38 extending over a length $L_M$ between the first end 22 and the opposing second end 24. More particularly, the body 38 extends from a first body end 38a to a second body end 38b, where the body ends 38a, 38b are just axially inward from the O-ring grooves 26 defined in mandrel 16. Further, the mandrel 16 has an inlet port 40 on one end 22, 24; the inlet port 40 is defined at the first end 22 in the illustrated embodiment. A fill port 42 is defined in the body 38 between the first end 22 and the second end 24; in the depicted embodiment, the fill port 42 is defined near the first end 22. In addition, a first bore 44 extends within the body 38 and is in fluid communication with the inlet port 40 and fill port 42.

More particularly, the first bore 44 extends coaxially with the central axis A of the elastomeric pump 10 from the first end 22 to the fill port 42, which extends transversely through the mandrel body 38. Fluid enters the elastomeric pump 10 through the mandrel inlet port 40 and flows through the fill port 42 into the reservoir formed by the bladder 14. To dispense the fluid from the reservoir, the fluid enters a dispense port 43 and flows through a second coaxial bore 46 to an outlet port 48 defined at or near the second end 24; the outlet port 48 is in fluid communication with the tube 34, which delivers the fluid to a patient. It will be appreciated that one or more check valves may be included in the infusion pump assembly, e.g., to prevent fluid from flowing from the reservoir back through the inlet port 40 or from prematurely flowing from the reservoir to the tube 34 for delivery to the patient.

The body 38 of mandrel 16 has an outer diameter $D_M$ that varies between the first end 22, a midpoint of the length $M_M$, and the second end 24. For instance, in the embodiment shown in FIGS. 3 and 4, the mandrel 16 has a first outer diameter $D_{M1}$ at the first body end 38a that is smaller or less than a midpoint outer diameter $D_{MM}$. The midpoint outer diameter $D_{MM}$ is smaller or less than a second outer diameter $D_{M2}$ at the second body end 38b. As such, the midpoint outer diameter $D_{MM}$ is different than the outer diameter at each of the first and second body ends 38a, 38b, and the mandrel 16 is generally tapered between the first and second ends 22, 24, e.g., mandrel 16 is tapered from the second body end 38b to the first body end 38a. That is, in the exemplary embodiment depicted in FIGS. 3 and 4, the outer diameter $D_M$ gradually increases from the first body end 38a to the second body end 38b or gradually decreases or tapers from the second body end 38b to the first body end 38a, such that the outer diameter $D_M$ is slightly smaller at each point along the mandrel body length $L_M$ from the second body end 38b to the first body end 38a. By tapering the outer diameter $D_M$ of mandrel 16 in the region of the fill port 42, which is defined near the first body end 38a in the depicted embodiment, the crack and fill pressure may be reduced due to a decrease in resistance the fluid must overcome to initiate filling the reservoir defined by the bladder 14. For example, the tapered mandrel 16 allows pre-stretching of the elastomeric bladder 14 across the working area of the elastomer, i.e., the pre-stretch may be tapered to match the way the balloon inflates and deflates. Further, the tapered mandrel 16 may encourage the reservoir to fill more evenly because the elastomeric reservoir elongation will begin near one end of the mandrel 16 and move toward the opposite end.

In other embodiments, the outer diameter $D_M$ may gradually decrease from the first body end 38a to the second body end 38b, such that the mandrel body 38 is tapered from the first body end 38a to the second body end 38b. Stated differently, the outer diameter $D_M$ may gradually increase from the second body end 38b to the first body end 38a. More specifically, the first outer diameter $D_{M1}$ at the first body end 38a may be greater or larger than the midpoint outer diameter $D_{MM}$, and in turn, the midpoint outer diameter $D_{MM}$ may be greater or larger than the second outer diameter $D_{M2}$ at the second body end 38b. As such, the midpoint outer diameter $D_{MM}$ is different than the outer diameter at each of the first and second body ends 38a, 38b, but unlike the embodiment depicted in FIGS. 3 and 4, the mandrel 16 is generally tapered from the first body end 38a to the second body end 38b. Accordingly, in such embodiments, the outer diameter $D_M$ gradually decreases from the first body end 38a to the second body end 38b such that the outer diameter $D_M$ is slightly smaller at each point along the mandrel body length $L_M$ from the first body end 38a to the second body end 38b.

Figure 5:
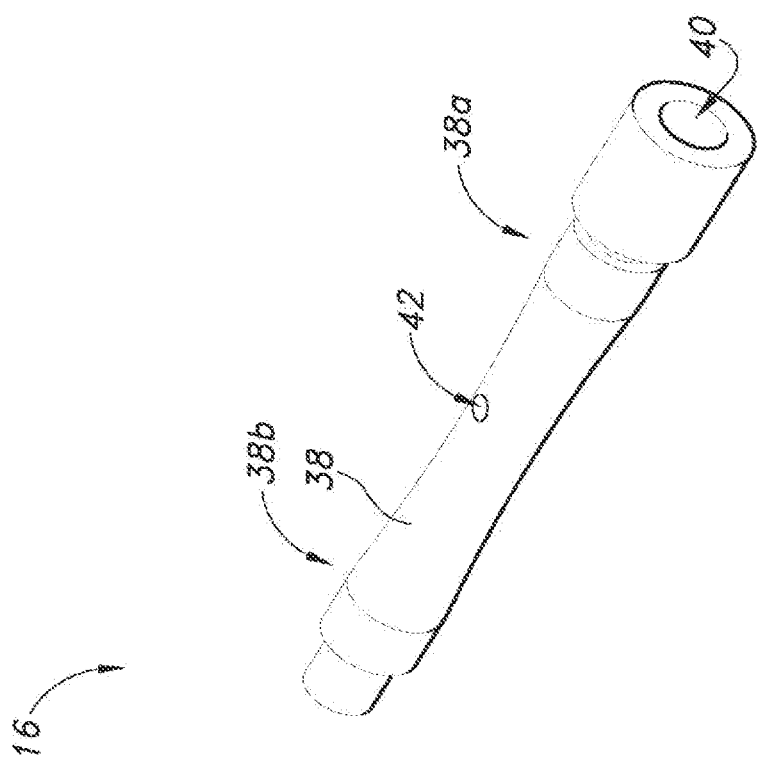
FIG. 5 is a perspective view of a mandrel of an infusion assembly according to an exemplary embodiment of the present subject matter.
Figure 6:
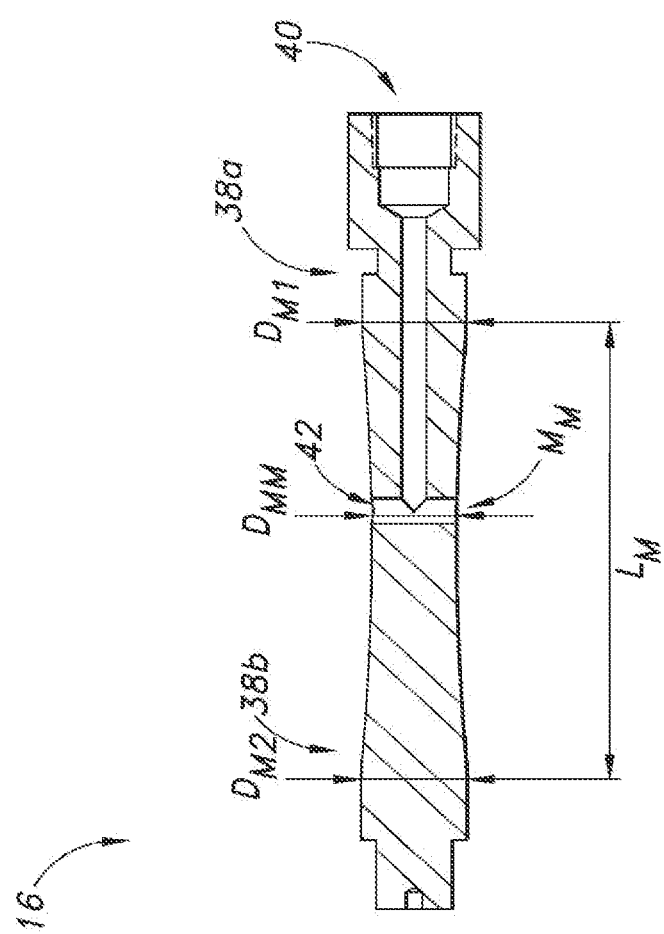
FIG. 6 is a cross-section view of the mandrel of FIG. 5.

Turning to FIGS. 5 and 6, a perspective view and a cross-section view are provided of a mandrel 16 according to another exemplary embodiment of the present subject matter. As shown in the depicted embodiment, the midpoint outer diameter $D_{MM}$ is less than the outer diameter at each of the first body end 38a and the second body end 38b such that the mandrel 16 is a generally concave mandrel. That is, the midpoint outer diameter $D_{MM}$ is smaller or less than both the first outer diameter $D_{M1}$ and the second outer diameter $D_{M2}$ such that the outer diameter $D_M$ tapers from each body end 38a, 38b toward the midpoint $M_M$ and is smaller in the middle of the mandrel body 38 than at either body end 38a, 38b. Further, the fill port 42 is defined generally at the midpoint $M_M$ of the mandrel body length $L_M$, where the mandrel diameter $D_M$ is the smallest.

Figure 7:
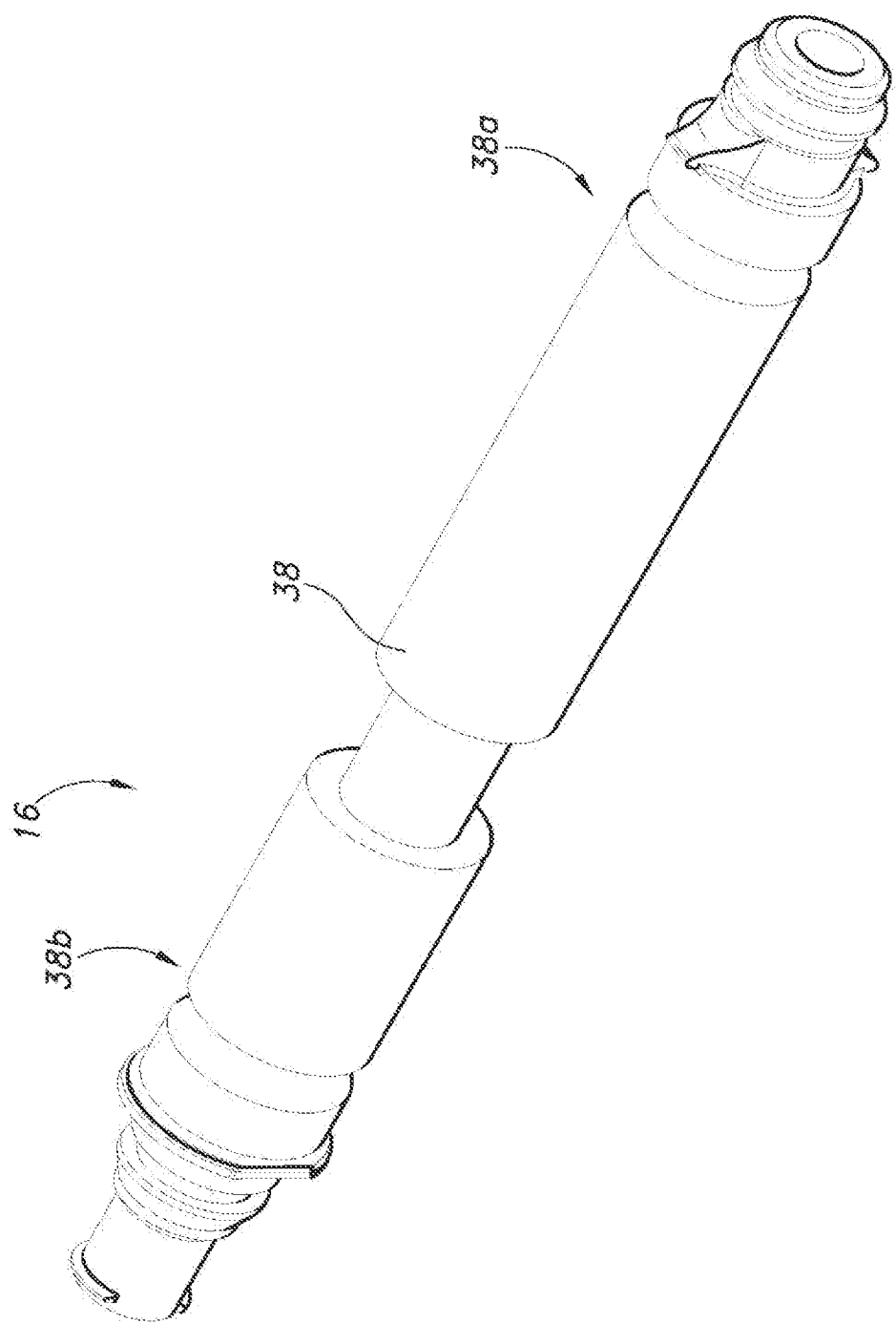
FIG. 7 is a perspective view of a mandrel of an infusion assembly according to an exemplary embodiment of the present subject matter.

FIG. 7 provides a perspective view of a mandrel 16 according to another exemplary embodiment of the present subject matter. Similar to the embodiment depicted in FIGS. 5 and 6, the mandrel 16 shown in FIG. 7 has a reduced outer diameter $D_M$ around the midpoint $M_M$ of the mandrel length $L_M$. However, unlike the embodiment of FIGS. 5 and 6, the mandrel depicted in FIG. 7 does not have a smoothly tapered outer diameter $D_M$. Rather, the outer diameter is stepped from the first diameter $D_{M1}$ to the midpoint diameter $D_{MM}$ and from the midpoint diameter $D_{MM}$ to the second diameter $D_{M2}$; in some embodiments, the first and second diameters $D_{M1}$, $D_{M2}$ may be substantially equal. Thus, as illustrated in FIG. 7, the outer diameter $D_M$ does not gradually or smoothly transition from one diameter to another but abruptly changes from one diameter to another.

Reducing outer diameter $D_M$ of the mandrel 16 around the port 42 defined in the mandrel body 38 defines a gap between an outer surface 50 of the mandrel 16 and the inner surface 36 of the bladder 14 around the port 42. The gap at the fill port 42 may reduce the crack and fill pressure of the elastomeric pump 10, as well as provide more uniform filling of the reservoir around the mandrel 16. Further, when the fill port 42 is defined at approximately the mandrel midpoint $M_M$, such that the gap is approximately centered with respect to mandrel body 38, the elastomeric pump 10 may experience more uniform, centered filling of the bladder reservoir.

Figure 8:
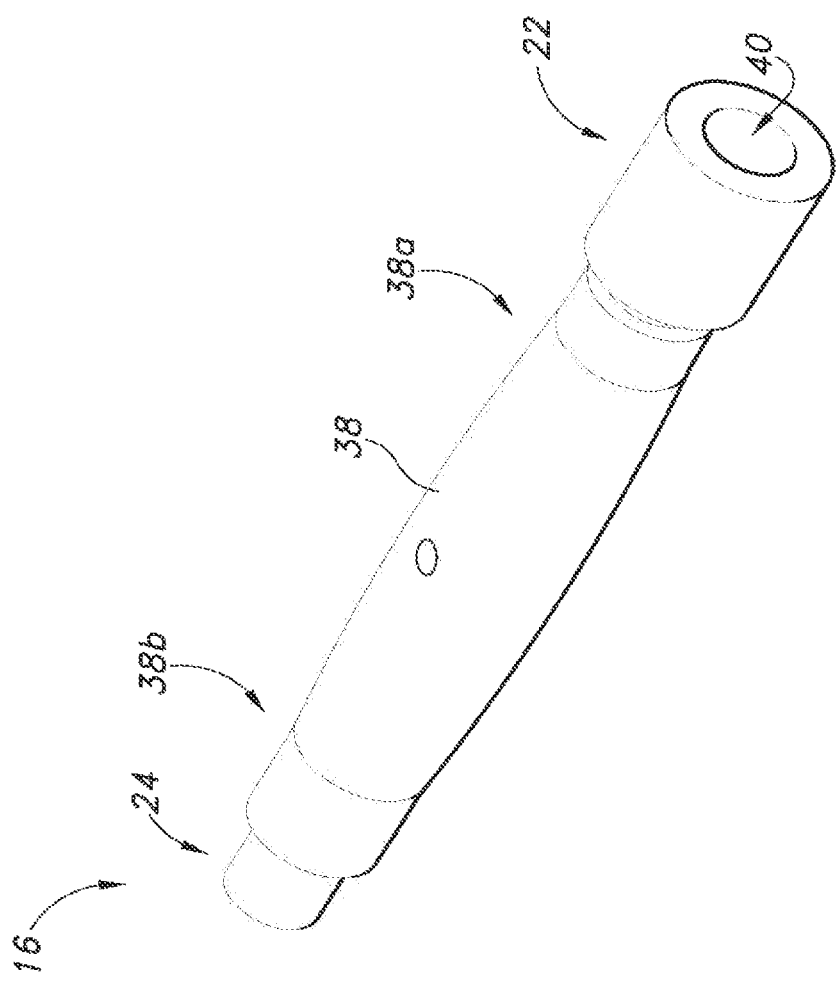
FIG. 8 is a perspective view of a mandrel of an infusion assembly according to an exemplary embodiment of the present subject matter.

In other embodiments, such as the embodiment of mandrel 16 illustrated in the perspective view of FIG. 8, the outer diameter $D_M$ may be increased or larger in the region of the midpoint $M_M$ compared to the first body end 38a and the second body end 38b, such that the mandrel 16 is a generally convex mandrel. That is, the midpoint outer diameter $D_{MM}$ is greater or larger than both the first outer diameter $D_{M1}$ and the second outer diameter $D_{M2}$ such that the outer diameter $D_M$ tapers from approximately the midpoint $M_M$ toward the body ends 38a, 38b and is smaller at the ends of the mandrel body 38 than in the midsection. The outer diameter $D_M$ may be substantially the same at each body end 38a, 38b and may gradually and smoothly transition from the largest diameter at or near the midpoint $M_M$ to the smaller diameters at each body end 38a, 38b. Further, the fill port 42 may be defined generally at the midpoint $M_M$ of the mandrel body length $L_M$, where the mandrel diameter $D_M$ is the largest.

By increasing the mandrel outer diameter $D_M$ in the midsection of the length $L_M$, the bladder 14 may be pre-stretched in a manner that tapers the pre-stretch across the working area of the elastomeric bladder in a way that matches the inflation and deflation of the bladder. As such, the pre-stretch mirrors the elastomer elongation, which is greatest in the midsection of the bladder 14 and tapers off toward the O-ring seals at the ends of the reservoir. Accordingly, the uniformity of the incremental pressure and/or flow rate may be increased. Moreover, the volume of fluid retained in the reservoir at the end of the infusion period may be reduced. More particularly, the increased mandrel outer diameter $D_M$ is the same location where the elastomeric bladder 14 stretches the most and, thus, has the greatest likelihood to retain fluid. By increasing the mandrel outer diameter $D_M$, part of the volume for retained fluid is instead occupied by the mandrel 16, thereby reducing the overall volume of fluid retained in the reservoir.

Figure 9:
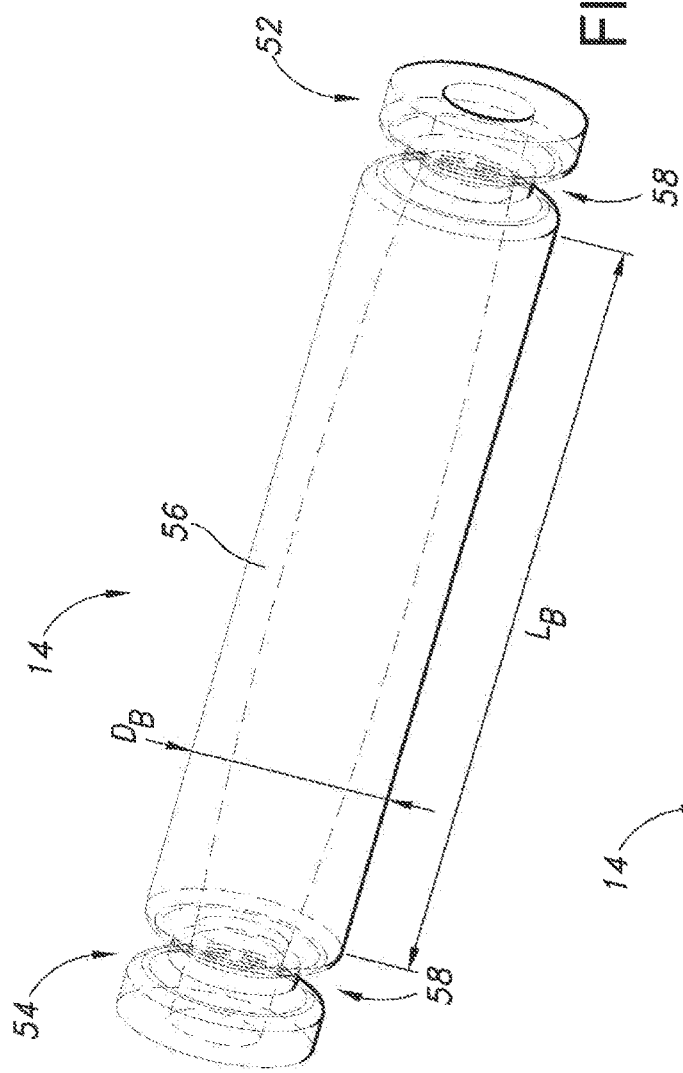
FIG. 9 is a perspective view of a bladder of an infusion assembly according to an exemplary embodiment of the present subject matter.
Figure 10:
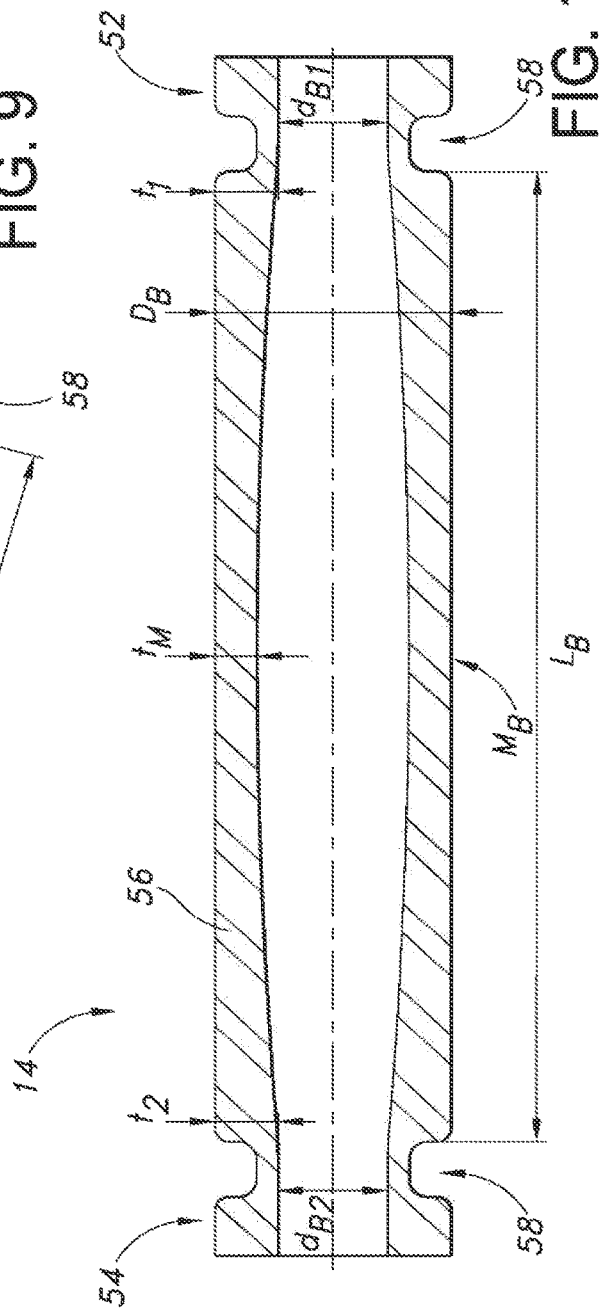
FIG. 10 is a cross-section view of the bladder of FIG. 9.

Referring now to FIGS. 9 and 10, a perspective view and a cross-section view are provided of a bladder 14 according to an exemplary embodiment of the present subject matter. Referring particularly to FIG. 9, the bladder 14 has a first end 52 and a second end 54; when assembled with a mandrel 16, the bladder first end 52 is positioned adjacent the mandrel first end 22 and the bladder second end 54 is positioned adjacent the mandrel second end 24. A body 56 of the bladder extends between the opposing bladder ends 52, 54, and the body 56 has a length $L_B$. The bladder body 56 has a generally constant outer diameter $D_B$ over the length $L_B$. As further illustrated in FIG. 9, each bladder end 52, 54 defines a groove 58 about its outer perimeter for receipt of an O-ring (not shown).

As most shown in the cross-section view of FIG. 10, the bladder 14 has a wall thickness t and an inner diameter $d_B$ that each vary along the length $L_B$. More particularly, the bladder 14 has a first inner diameter $d_{B1}$ at the first end 52 that is smaller or less than a midpoint inner diameter $d_{BM}$. The midpoint inner diameter $d_{BM}$ is greater or larger than a second inner diameter $d_{B2}$ at the second end 54. As such, the midpoint inner diameter $d_{BM}$ is different than the inner diameter at each of the first and second ends 52, 54, although the first inner diameter $d_{B1}$ may be substantially equal to the second inner diameter $d_{B2}$. Because the bladder outer diameter $D_B$ remains substantially constant along the length $L_B$, the varying bladder inner diameter $d_B$ indicates the wall thickness t of the bladder 14 varies along the length $L_B$. More specifically, the bladder wall thickness t is generally tapered from the midpoint $M_B$ to each of the first end 52 and second end 54, i.e., the bladder 14 has a midpoint wall thickness $t_M$ at the midpoint $M_B$, a first wall thickness $t_1$ at the first end 52, and a second wall thickness $t_2$ at the second end 54. The inner diameter $D_B$ gradually decreases or tapers from the midpoint $D_B$ to the ends 52, 54, such that the inner diameter $D_B$ is slightly smaller at each point along the bladder body length $L_B$ from the midpoint $D_B$ to the first end 52 and from the midpoint $D_B$ to the second end 54. Stated differently, the wall thickness t is tapered toward the midpoint $M_B$, i.e., the wall thickness t decreases from each end 52, 54 toward the midpoint $M_B$. Further, the wall thickness t is greatest, i.e., the bladder 14 is thickest at each end 52, 54. The thickness of bladder 14 at ends 52, 54 helps ensure there is adequate bladder material at the ends 52, 54 to define grooves 58.

A decreased bladder wall thickness $t_M$ in the bladder midsection helps to promote uniform filling of the reservoir formed by the bladder 14 when the fill port 42 is aligned with the thinner bladder midsection, e.g., by creating a path of least resistance at the midsection, where there is less material force to overcome to initiate filling because of the decreased wall thickness t. Uniform filling may aid in providing a more consistent pressure and flow rate as the reservoir empties during the infusion.

Figure 12:
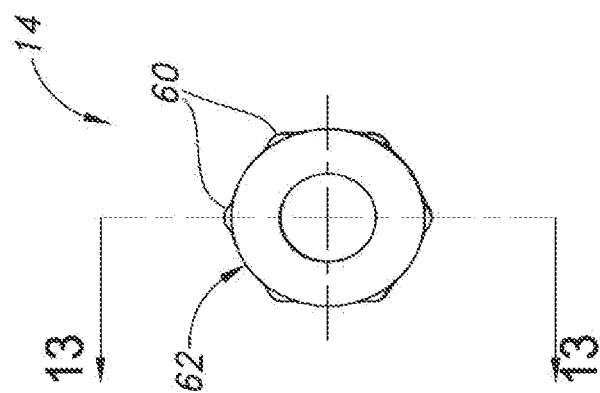
FIG. 12 is an end view of the bladder of FIG. 11.
Figure 11:
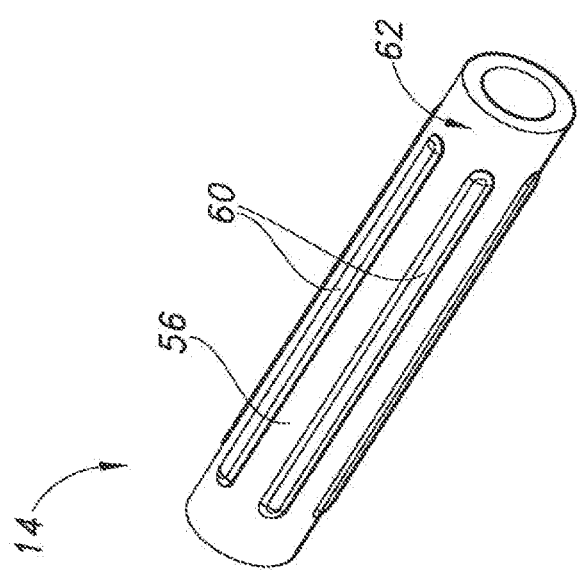
FIG. 11 is a perspective view of a bladder of an infusion assembly according to an exemplary embodiment of the present subject matter.

FIGS. 11 and 12 provide a perspective view and an end view of a bladder 14 according to another exemplary embodiment of the present subject matter. As shown in the depicted embodiment, a plurality of ribs 60 may be defined along an outer surface 62 of the bladder 14. The ribs 60 may be evenly spaced apart from one another about a circumference of the bladder or may have any other suitable configuration. The ribs 60 may be formed from the material from which the bladder 14 is made such that the ribs 60 and bladder 14 are one integral component.

Figure 13:
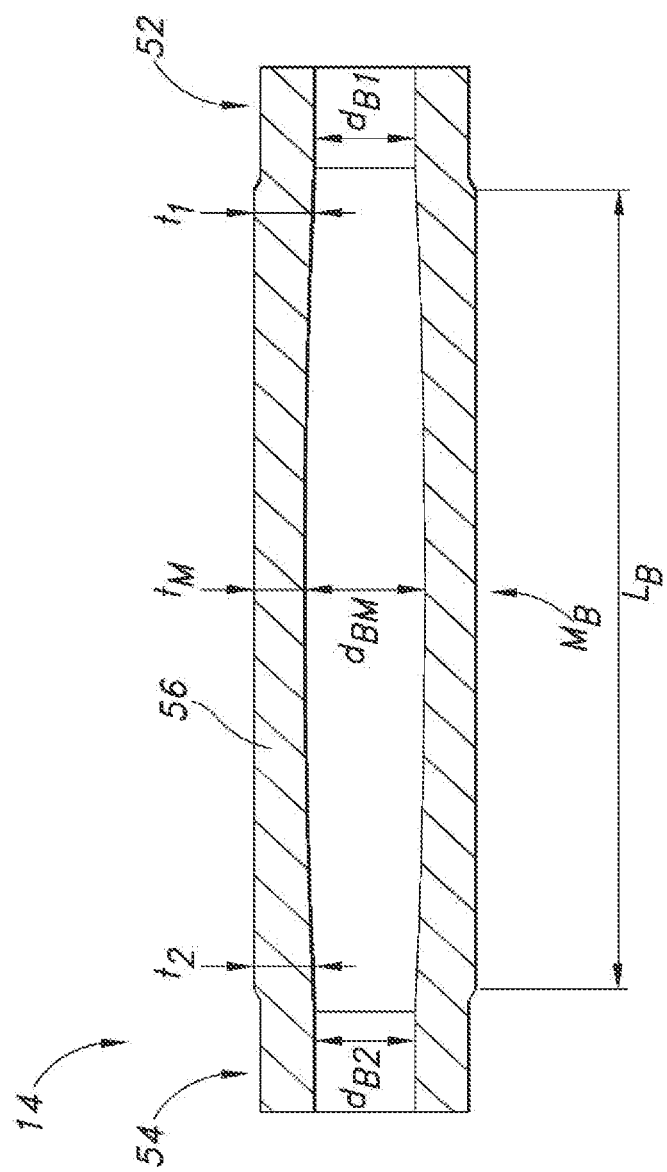
FIG. 13 is a cross-section view of the bladder of FIG. 11 according to an exemplary embodiment of the present subject matter.
Figure 14:
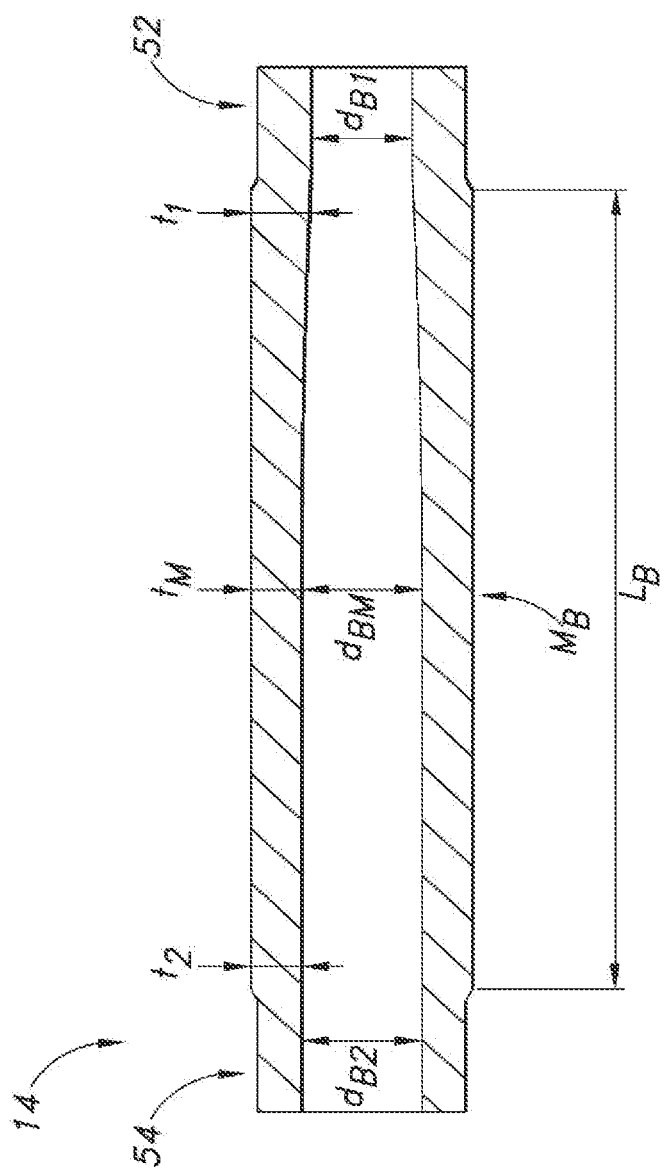
FIG. 14 is a cross-section view of the bladder of FIG. 11 according to another exemplary embodiment of the present subject matter.

FIGS. 13 and 14 provide cross-section views of the bladder 14 of FIGS. 11 and 12 according to two exemplary embodiments of the present subject matter. Turning first to FIG. 13, the bladder 11 of FIGS. 11 and 12 may have a wall thickness t and inner diameter $d_B$ that each vary similarly to the bladder 14 depicted in FIGS. 9 and 10. That is, the bladder 14 illustrated in FIG. 13 has a first inner diameter $d_{B1}$ at the bladder first end 52 that is smaller or less than a midpoint inner diameter $d_{BM}$. The midpoint inner diameter $d_{BM}$ is greater or larger than a second inner diameter $d_{B2}$ at the second end 54. As such, the midpoint inner diameter $d_{BM}$ is different than the inner diameter at each of the first and second ends 52, 54, although the first inner diameter $d_{B1}$ may be substantially equal to the second inner diameter $d_{B2}$. Further, the wall thickness t of the bladder 14 varies along the length $L_B$. More specifically, the bladder wall thickness t is generally tapered from the midpoint $M_B$ to each of the first end 52 and second end 54, i.e., the bladder 14 has a midpoint wall thickness $t_M$ at the midpoint $M_B$, a first wall thickness $t_1$ at the first end 52, and a second wall thickness $t_2$ at the second end 54. The inner diameter $d_B$ gradually decreases or tapers from the midpoint $M_B$ to the ends 52, 54, such that the inner diameter $d_B$ is slightly smaller at each point along the bladder body length $L_B$ from the midpoint $M_B$ to the first end 52 and from the midpoint $M_B$ to the second end 54. Stated differently, the wall thickness t is tapered toward the midpoint $M_B$, i.e., the wall thickness t decreases from each end 52, 54 toward the midpoint $M_B$. As such, the wall thickness t is greatest, i.e., the bladder 14 is thickest at each end 52, 54. Tapering the bladder wall thickness $t_1$n the midsection as shown in FIGS. 9, 10, and 13 may have several benefits, as described in greater detail above.

As illustrated in FIG. 14, in other embodiments, the bladder wall thickness t may be tapered from one end of the bladder 14 to the other. More particularly, the bladder 14 has a first inner diameter $d_{B1}$ at the first end 52 that is greater or larger than a midpoint inner diameter $d_{BM}$. The midpoint inner diameter $d_{BM}$ is greater or larger than a second inner diameter $d_{B2}$ at the second end 54. As such, the midpoint inner diameter $d_{BM}$ is different than the inner diameter at each of the first and second ends 52, 54, and the bladder inner diameter is generally tapered from the first end 52 to the second end 54. In the exemplary embodiment depicted in FIG. 14, the inner diameter $d_B$ gradually decreases or tapers from the first end 52 to the second end 54, such that the inner diameter $d_B$ is slightly smaller at each point along the bladder body length $L_B$ from the first end 52 to the second end 54.

Further, the bladder wall thickness t is different at each point from the first end 52 to the second end 54, and more specifically, the wall thickness t increases from the first end 52 to the second end 54. As shown in FIG. 14, the wall thickness t gradually and smoothly increases from the first end 52 to the second end 54. Described differently, the wall thickness t is tapered from the second end 54 to the first end 52, i.e., the wall thickness t gradually decreases from the second end 54 of bladder 14 to the first end 52 of bladder 14. Accordingly, the bladder 14 is thinnest at the first end 52, where the wall thickness t is the smallest or least, and thickest at the second end 54, where the wall thickness t is the largest or greatest.

By tapering the wall thickness t as shown in FIG. 14 and aligning the fill port 42 with the thinnest part of the bladder 14, the reservoir formed by the bladder 14 may more uniformly fill with fluid. As previously described, the thinnest bladder wall section provides a path of least resistance because, compared to sections where the bladder is thicker, there is less material force to overcome to initiate filling. As such, the crack pressure of the pump 10 may be lowered.

Further, uniform filling also may help provide a more consistence pressure and flow rate as the reservoir empties during an infusion procedure.

In some embodiments, the bladder 14 may be made from a silicone or a polyisoprene material. For instance, an appropriate silicone or polyisoprene material may be one that forms inflatable tubes; results in a maximum pressure, as measured a short distance downstream of the first port, within a desired range when inflated with a predetermined volume of liquid; and provides sufficient constricting forces to expel substantially all the liquid. Of course, other materials also may be suitable for forming bladder 14. Further, an exemplary range of wall thicknesses t for bladder 14 is from about 0.075 inches up to about 0.180 inches. An exemplary range of the inner diameters $d_B$ of bladder 14 is from approximately 0.355 inches to approximately 0.600 inches. Various combinations of bladder length $L_B$, wall thickness t, inner diameter $d_B$, and suitable materials may yield bladders having fill volumes in the range of about 50 to about 600 ml of liquid.

Moreover, suitable combinations of the mandrels 16 and bladders 14 described herein may be used to optimize the performance of elastomeric infusion pump 10. For example, a bladder 14 described in the above exemplary embodiments may be secured to a mandrel 16 described in the above exemplary embodiments. In other embodiments, an exemplary bladder 14 described above may be secured to a known mandrel, or a known bladder may be secured to an exemplary mandrel 16 described above, to form an elastomeric infusion pump 10. The bladder and mandrel combination may be selected to minimize crack pressure, have less variability in the flow profile of the infusion pump 10, and/or have a higher flow rate accuracy. Other advantages also may be realized by using one or more of the configurations described herein.

Figure 15:
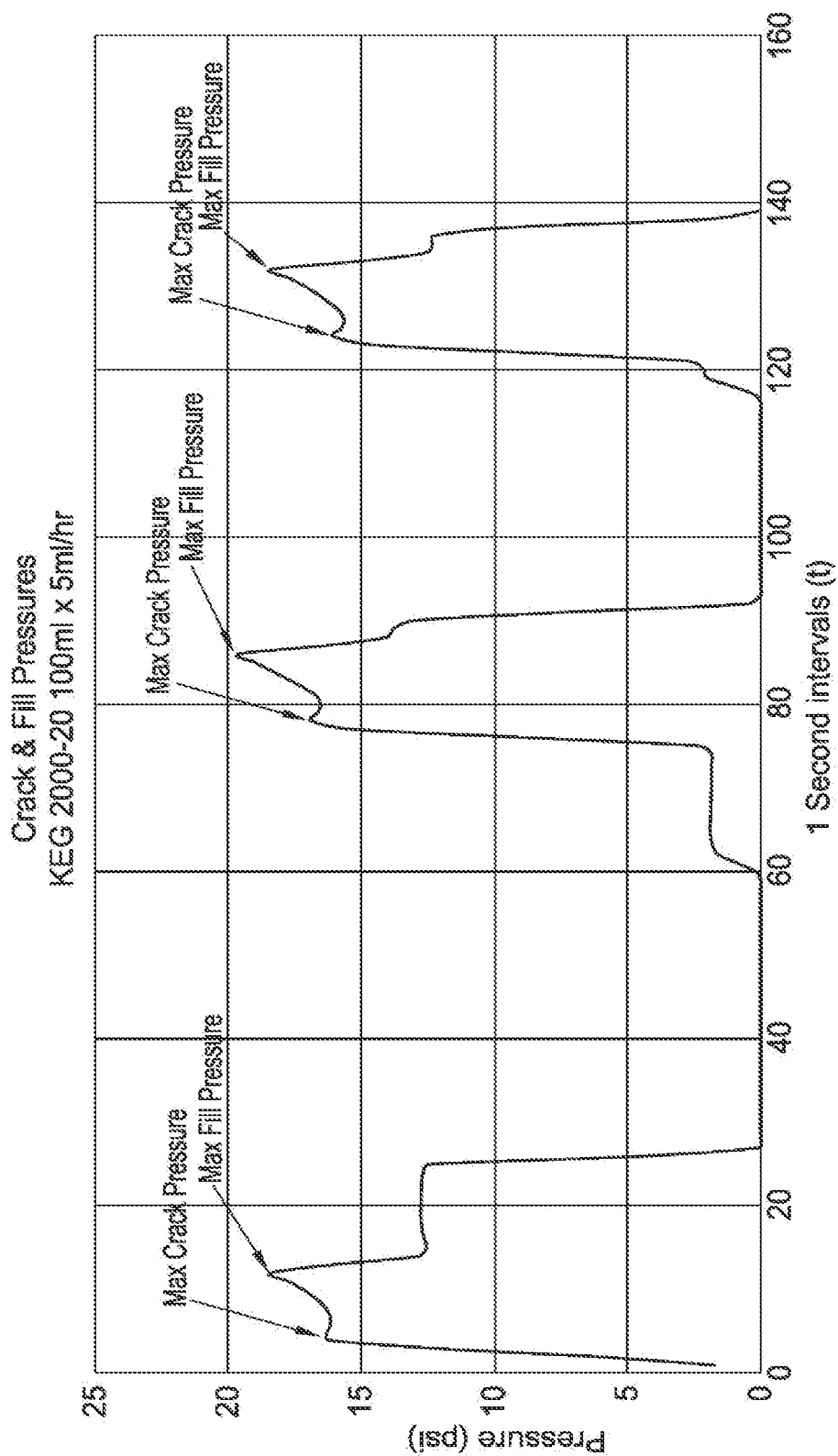
FIG. 15 provides a graph of crack and fill pressures for a bladder formed according to an exemplary embodiment of the present subject matter and disposed on a mandrel having a known configuration.
Figure 16:
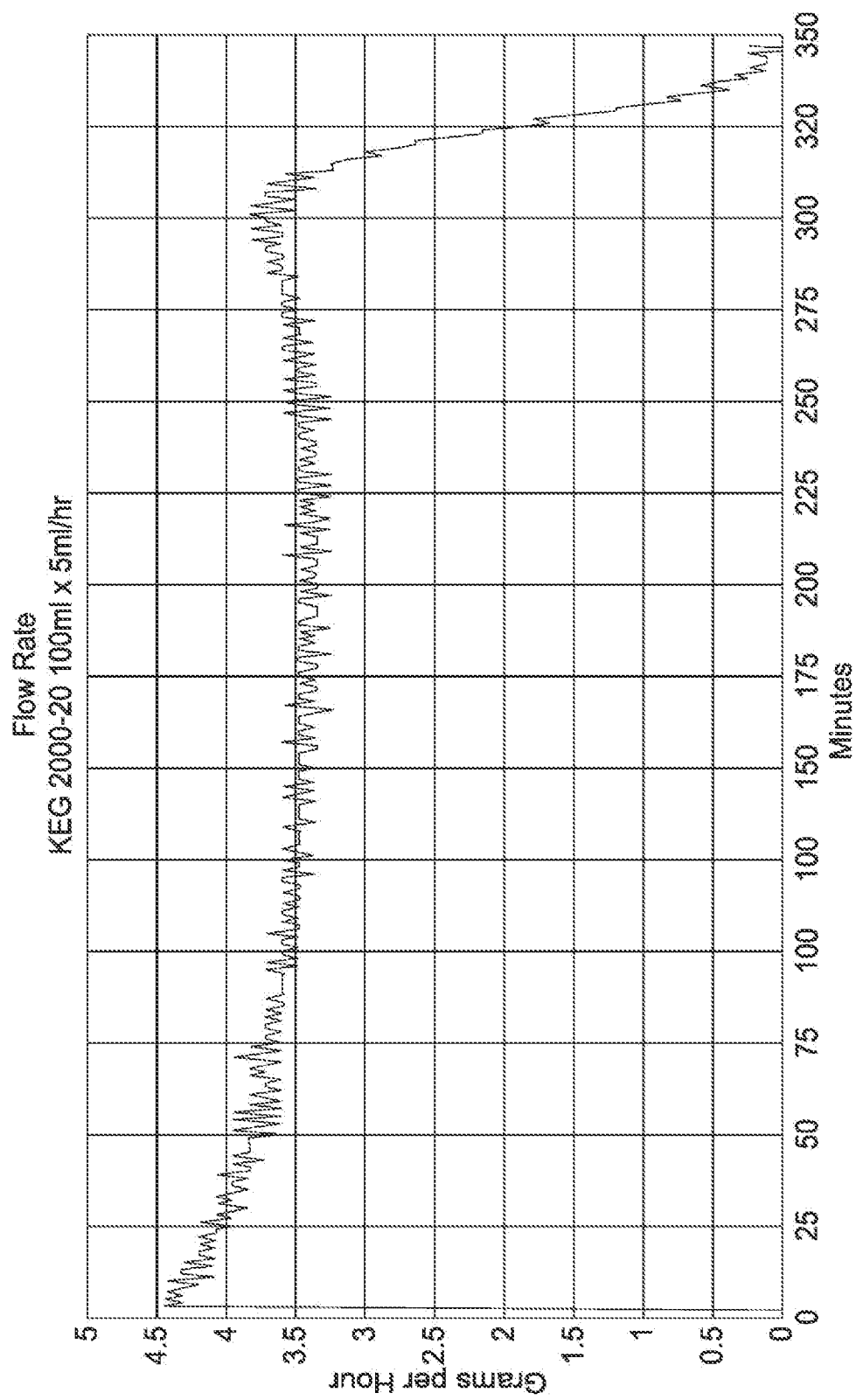
FIG. 16 provides a graph of the flow rate for a bladder formed according to an exemplary embodiment of the present subject matter and disposed on a mandrel having a known configuration.

FIG. 15 provides a graph of crack and fill pressures, and FIG. 16 provides graph of the flow rate for an exemplary bladder 14 disposed on a mandrel having a known configuration. More specifically, FIGS. 15 and 16 provide graphs of data for a bladder 14 made from a silicone elastomer KEG 2000-20 and configured as shown and described with respect to FIG. 13. For the data sets illustrated in FIGS. 15 and 16, the bladder 14 has a fill volume of 100 ml and an infusion rate of 5 ml/hour.

As shown in FIG. 15, the exemplary bladder 14 has a maximum crack pressure and a maximum fill pressure for each cycle, and the maximum crack and fill pressures are below 20 psig. FIG. 16 depicts that the flow rate of fluid from the bladder 14 eventually decays to approximately zero (0) grams/hour as the bladder 14 empties, but the flow rate remains substantially steady, gradually transitioning from a first flow rate to a second flow rate, which are within about one (1) gram/hour of one another, as the fluid is dispensed from the bladder 14. Accordingly, FIGS. 15 and 16 provide an example that bladders 14 made as described herein may have lower crack and fill pressures and more uniform flow rates compared to known bladders and elastomeric pump configurations.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. An elastomeric pump, comprising:
   an expandable bladder extending longitudinally between opposing first and second connecting end portions, the bladder extending longitudinally from a first end adjacent the first connecting end portion of the bladder to an opposing second end adjacent the second connecting end portion of the bladder, and
   a mandrel extending within the bladder, the mandrel including a fill port for providing a fluid to expand the bladder, the fill port provided on a concave surface outer surface of the mandrel,
   wherein the bladder only expands in a radial direction.

2. The elastomeric pump of claim 1, further comprising a plurality of ribs projecting from and longitudinally along an outer surface of the bladder along a length of the bladder.

3. The elastomeric pump of claim 1, wherein an outer surface of the bladder includes a first decreasing tapered segment between the bladder and the first connecting end portion and a second decreasing tapered segment between the bladder and the second connecting end portion.

4. The elastomeric pump of claim 1, wherein at least portion of an outer diameter of each of the first and second connecting end portions is less than an outer diameter of the bladder.

5. The elastomeric pump of claim 1, wherein the bladder further includes an outer diameter, an inner diameter, and a wall thickness defined between the inner and outer diameter,
   wherein the wall thickness gradually decreases from a first wall thickness at the first end to a second, smaller, wall thickness proximate the fill port,
   wherein an inner diameter at the first connecting end portion varies from an inner diameter of the bladder.

6. An elastomeric pump, comprising:
   an expandable bladder extending longitudinally between opposing first and second connecting end portions, where at least portion of an outer diameter of each of the first and second connecting end portions is less than an outer diameter of the bladder, the bladder extending longitudinally from a first end adjacent the first connecting end portion of the bladder to an opposing second end adjacent the second connecting end portion of the bladder, the bladder including an outer diameter, an inner diameter, and a wall thickness defined between the inner and outer diameter,
   a mandrel extending within the bladder, the mandrel including a fill port for providing a fluid to expand the bladder, the fill port defined at an intermediate portion of the mandrel, an outer diameter of the mandrel gradually transitioning to a lesser outer diameter at the fill port,
   wherein a wall thickness at a midpoint of the length of the bladder is less than a wall thickness at each of the first second ends of the bladder, such that the wall thickness of the bladder tapers gradually from the first and second ends toward the midpoint.

7. The elastomeric pump of claim 6, further comprising a plurality of ribs projecting from and longitudinally along an outer surface of the bladder along a length of the bladder.

8. The elastomeric pump of claim 6, wherein at least portion of an outer diameter of each of the first and second connecting end portions is less than an outer diameter of the bladder.

9. The elastomeric pump of claim 6, wherein the fill port is provided at a midpoint of the mandrel, wherein the bladder is configured to receive a fluid at the midpoint because the wall thickness at the midpoint is less than the wall thickness at each of the first end and the second end such that there is less material force to overcome to initiate filing of the bladder because of the decreased wall thickness at the midpoint.

10. The elastomeric pump of claim 6, wherein the portions of each of the first connecting end portion and the second connecting end portion that are less than an outer diameter of the bladder define a groove about an outer perimeter of the bladder for receipt of an O-ring configured for securing the bladder to a mandrel.

11. An elastomeric pump for an infusion assembly, the elastomeric pump comprising:
    an inflatable elastomeric bladder comprising:
       an expandable body extending longitudinally between opposing first and second connecting end portions, where at least a portion of an outer diameter of each of the first and second connecting end portions is less than an outer diameter of the body,
       the body extending longitudinally over a bladder length from a first bladder end adjacent the first connecting end portion to an opposing second bladder end adjacent the second connecting end portion, the body further including:
          a central lumen defined by an inner surface of the bladder,
          a bladder outer diameter,
          a bladder inner diameter measured at the inner surface, and
          a wall thickness defined between the bladder outer diameter and bladder inner diameter; and
    a mandrel extending within the central lumen of the bladder, the mandrel defining a mandrel port in fluid communication with the central lumen of the bladder, the mandrel port disposed adjacent a midpoint of the bladder length,
    wherein the bladder is disposed on the mandrel such that the bladder is sealingly secured on the mandrel at the first and second connecting end portions,
    wherein the body expands only in a radial direction, and
    wherein the bladder is configured to receive a fluid from the mandrel port adjacent the midpoint of the bladder length, wherein the wall thickness at the midpoint is less than the wall thickness at each of the first and second ends such that there is less material force to overcome to initiate filling because of the decreased wall thickness at the midpoint.

12. The elastomeric pump of claim 11, wherein the wall thickness at the first bladder end is greater than the wall thickness at the second bladder end.

13. The elastomeric pump of claim 11, wherein the wall thickness at the second bladder end is greater than the wall thickness at the first bladder end.

14. The elastomeric pump of claim 11, wherein the mandrel comprises:
    a mandrel body extending over a mandrel length from a first mandrel end to an opposing second mandrel end; and
    a mandrel outer diameter.

15. The elastomeric pump of claim 14, wherein the mandrel outer diameter at a midpoint of the mandrel length is less than the mandrel outer diameter at each of the first mandrel end and the second mandrel end such that the mandrel is a generally concave mandrel.

16. The elastomeric pump of claim 15, wherein the wall thickness of the bladder at the midpoint of the bladder length is less than the wall thickness at each of the first bladder end and the second bladder end such that the wall thickness tapers from each of the first bladder end and the second bladder end toward the midpoint of the bladder length.

17. The elastomeric pump of claim 11, wherein the portions of each of the first connecting end portion and the second connecting end portion that are less than an outer diameter of the bladder define a groove about an outer perimeter of the bladder for receipt of an O-ring that secures the bladder to the mandrel.

18. The elastomeric pump of claim 11, wherein the bladder further comprises a plurality of ribs projecting from and longitudinally along an outer surface of the bladder.

19. An elastomeric pump for an infusion assembly, the elastomeric pump comprising:
 an inflatable elastomeric bladder comprising:
  an expandable body extending longitudinally between opposing first and second connecting end portions, where at least a portion of an outer diameter of each of the first and second connecting end portions is less than an outer diameter of the body,
  the body extending longitudinally over a bladder length from a first bladder end adjacent the first connecting end portion to an opposing second bladder end adjacent the second connecting end portion, the body further including:
   a central lumen defined by an inner surface of the bladder,
   a bladder outer diameter,
   a bladder inner diameter measured at the inner surface, and
   a wall thickness defined between the bladder outer diameter and bladder inner diameter; and
  a mandrel extending within the central lumen of the bladder, the mandrel defining a mandrel port in fluid communication with the central lumen of the bladder, the mandrel port disposed adjacent a midpoint of the bladder length,
 wherein the bladder is disposed on the mandrel such that the bladder is sealingly secured on the mandrel at the first and second connecting end portions, wherein the body expands only in a radial direction, and
 wherein the mandrel outer diameter at a midpoint of the mandrel length is less than the mandrel outer diameter at each of the first mandrel end and the second mandrel end such that the mandrel is a generally concave mandrel.

20. The elastomeric pump of claim 19, wherein the wall thickness of the bladder at the midpoint of the bladder length is less than the wall thickness at each of the first bladder end and the second bladder end such that the wall thickness tapers from each of the first bladder end and the second bladder end toward the midpoint of the bladder length.

* * * * *